US011622197B2

(12) United States Patent
Nejat et al.

(10) Patent No.: US 11,622,197 B2
(45) Date of Patent: Apr. 4, 2023

(54) AUDIO ENHANCEMENT FOR HEARING IMPAIRED IN A SHARED LISTENING ENVIRONMENT

(71) Applicant: SONY GROUP CORPORATION, Tokyo (JP)

(72) Inventors: Mahyar Nejat, San Diego, CA (US); Brant Candelore, San Diego, CA (US); Peter Shintani, San Diego, CA (US)

(73) Assignee: SONY GROUP CORPORATION, Tokyo (JP)

( * ) Notice: Subject to any disclaimer, the term of this patent is extended or adjusted under 35 U.S.C. 154(b) by 200 days.

(21) Appl. No.: 17/006,476

(22) Filed: Aug. 28, 2020

(65) Prior Publication Data

US 2022/0070583 A1 Mar. 3, 2022

(51) Int. Cl.
*H04R 5/04* (2006.01)
*G06T 7/00* (2017.01)
*H04R 3/04* (2006.01)
*H04R 5/033* (2006.01)
*H04R 29/00* (2006.01)
*H04S 1/00* (2006.01)
*H04W 72/12* (2023.01)
*H04L 65/75* (2022.01)

(52) U.S. Cl.
CPC ............ *H04R 5/04* (2013.01); *G06T 7/0012* (2013.01); *H04L 65/75* (2022.05); *H04R 3/04* (2013.01); *H04R 5/033* (2013.01); *H04R 29/001* (2013.01); *H04S 1/007* (2013.01); *H04W 72/1236* (2013.01); *G06T 2207/30196* (2013.01); *H04R 2430/01* (2013.01)

(58) Field of Classification Search
None
See application file for complete search history.

(56) References Cited

U.S. PATENT DOCUMENTS 7,212,247 B2  5/2007  Albean
7,742,740 B2  6/2010  Golderg et al.
(Continued)

FOREIGN PATENT DOCUMENTS

CN   103002378 A   3/2013
GB    2469793 A   11/2010
(Continued)

OTHER PUBLICATIONS

International Search Report and Written Opinion of PCT Application No. PCT/IB2021/057837, dated Jan. 27, 2022, 18 pages of ISRWO.

*Primary Examiner* — Antim G Shah
(74) *Attorney, Agent, or Firm* — Chip Law Group

(57) ABSTRACT

An electronic apparatus and method for enhancement of audio for users with a hearing impairment in a shared listening environment is provided. The electronic apparatus receives first audio content from a media source and detects a first user with a hearing disability as a wearer of the personal listening device. The electronic apparatus modifies one or more features of the first audio content based on an audio enhancement profile associated with the detected first user. Thereafter, the electronic apparatus generates second audio content based on the modification and shares the generated second audio content with the personal listening device.

18 Claims, 6 Drawing Sheets

(56) References Cited

U.S. PATENT DOCUMENTS

| | | | |
|---|---|---|---|
| 2013/0058503 A1* | 3/2013 | Kato | H04R 3/04 |
| | | | 381/107 |
| 2015/0062429 A1* | 3/2015 | Barbulescu | H04N 21/8106 |
| | | | 348/515 |
| 2015/0195661 A1 | 7/2015 | Neumann et al. | |
| 2018/0231944 A1* | 8/2018 | Johnston | H04N 21/43076 |
| 2018/0249263 A1* | 8/2018 | Raz | A61B 5/121 |

FOREIGN PATENT DOCUMENTS

| JP | 2013-057705 A | 3/2013 |
|---|---|---|
| WO | 2014/006220 A1 | 1/2014 |
| WO | 2014/040667 A1 | 3/2014 |

* cited by examiner

US 11,622,197 B2

AUDIO ENHANCEMENT FOR HEARING IMPAIRED IN A SHARED LISTENING ENVIRONMENT

CROSS-REFERENCE TO RELATED APPLICATIONS/INCORPORATION BY REFERENCE

None.

FIELD

Various embodiments of the disclosure relate to an assistive technology for people with disabilities. More specifically, various embodiments of the disclosure relate to an electronic apparatus for enhancement of audio for a hearing impaired in a shared listening environment.

BACKGROUND

Media devices, such as televisions, are typically capable of playing audio through various types of audio devices, such as through in-build speakers, wireless speakers, or wired/wireless headphones. Many media devices typically do not allow simultaneous output of sound in configurations, such as internal speakers and Bluetooth®, internal speakers and headphone jacks, headphone jacks and Bluetooth®, or Internal speakers, headphone jacks, and Bluetooth®. Thus, in a shared listening environment, if a user with a hearing disability wears an audio device, such as a wireless headphone, it is possible that the user may experience a poor audibility of the audio output from the audio device.

In some instances, the processing of wireless audio can take more time on the audio device. As a result, it is possible that the user with the hearing disability may experience an echo. In some other instances, while viewing video content, it is also possible that the user may experience lip-sync issues where the audio for the video content may be delayed in comparison to the video content. With such issues, the user may have a poor listening experience in comparison to other users with the normal hearing levels in the shared listening environment.

Limitations and disadvantages of conventional and traditional approaches will become apparent to one of skill in the art, through comparison of described systems with some aspects of the present disclosure, as set forth in the remainder of the present application and with reference to the drawings.

SUMMARY

An electronic apparatus and method for enhancement of audio for a hearing impaired in a shared listening environment is provided substantially as shown in, and/or described in connection with, at least one of the figures, as set forth more completely in the claims.

These and other features and advantages of the present disclosure may be appreciated from a review of the following detailed description of the present disclosure, along with the accompanying figures in which like reference numerals refer to like parts throughout.

DETAILED DESCRIPTION

The following described implementations may be found in the disclosed electronic apparatus and method to provide enhanced audio content for a user with a hearing disability in a shared listening environment. Exemplary aspects of the disclosure provide an electronic apparatus (for example, a smart television or any media player) which may receive audio content from a media source and may enhance the received audio content based on an audio enhancement profile of the user with the hearing disability. In a shared listening environment, conventional media devices play audio through connected audio devices to create a shared listening experience for all the users in the shared listening environment. While users with normal hearing levels (e.g., users. with a minimum to no hearing loss) may have a pleasant listening experience with the audio, users with a hearing disability may not be able to share the same experience. The reason for this may be attributed to audio characteristics of the played audio, as such characteristics are typically optimized only for users with normal hearing levels. In order to enhance the listening experience of the user with the hearing disability, the disclosed electronic apparatus may receive source audio content from a media source and may detect the user with a hearing disability as a wearer of a personal listening device (e.g., a wireless headphone). After such detection, the electronic apparatus may modify certain features (e.g., hearing levels (in dB) of certain audio frames) of the source audio content based on an audio enhancement profile associated with the detected first user to generate enhanced audio content, which may be optimized for the user with the hearing disability. The electronic apparatus may share the enhanced audio content with the personal listening device for playback so that the user with the hearing disability may have the same listening experience as that of the users with the normal hearing levels. The enhanced audio content may improve one or more of speech intelligibility, hearing comfort, sound quality, audibility across a broad range of frequencies, or perception of natural loudness of sound associated with the first audio content.

Figure 1:
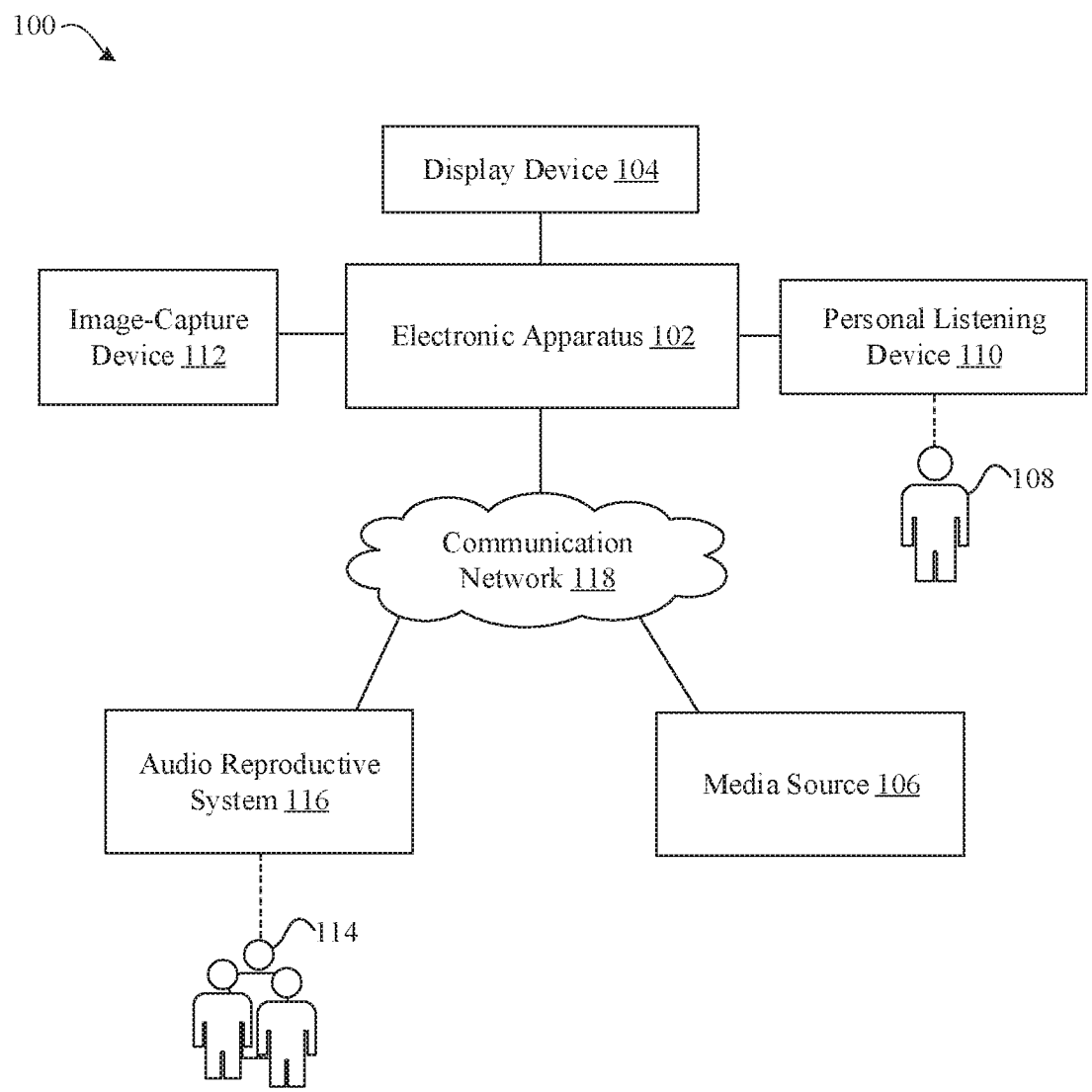
FIG. 1 is a diagram of an exemplary listening environment for users with normal hearing levels and with hearing disability, in accordance with an embodiment of the disclosure.

FIG. 1 is a diagram of an exemplary listening environment for users with normal hearing levels and with hearing disability, in accordance with an embodiment of the disclosure. With reference to FIG. 1, there is shown a listening environment 100 that includes an electronic apparatus 102, a display device 104, a media source 106, a first user 108, a personal listening device 110 for the first user 108, an image-capture device 112, a second user 114, and an audio reproductive system 116 for the second user 114. The electronic apparatus 102 may communicate with other electronic devices, such as the display device 104, the media source 106, the personal listening device 110, or the image-capture device 112, through a communication network 118. In some embodiments, one or more devices, such as the display device 104 and the image-capture device 112, may be communicatively coupled to the electronic apparatus 102, through Input-Output (IO) ports of the electronic apparatus 102.

The listening environment 100 may be a shared listening environment that may facilitate playback of enhanced audio content for users (such as the first user 108) with hearing disability, without affecting a listening experience of other users (such as the second user 114) with normal hearing levels in the listening environment 100. Examples of the listening environment 100 may include, but are not limited to, a cinema hall, a conference hall, a concert hall, an auditorium, or a home environment with shared audio/video resources among friends and family members.

The electronic apparatus 102 may include suitable logic, circuitry, and interfaces that may be configured to receive first audio content from the media source 106 and may modify certain features of the first audio content based on an audio enhancement profile of the first user 108 to generate second audio content. For example, a feature of the first audio content may include a signal energy levels or amplitude levels of a band of audible frequencies in audio frames of the first audio content. The second audio content may be shared with the personal listening device 110, which may be worn by the first user 108.

In an embodiment, the electronic apparatus 102 may be a portable media player that may be configured to communicate with the display device 104, via a wired or a wireless connection. Examples of such an implementation of the electronic apparatus 102 may include, but are not limited to, a digital media player (DMP), a micro-console, a TV tuner (such as an Advanced Television Systems Committee (ATSC) tuner), a set-top-box, an Over-the-Top (OTT) player, a digital media streamer, a media extender/regulator, or a digital media hub.

In another embodiment, the electronic apparatus 102 may be a display-enabled media player. In such a case, the entire functionality of the display device 104 may be incorporated in the electronic apparatus 102, without a deviation from scope of the disclosure. Examples of such an implementation of the electronic apparatus 102 may include, but are not limited to, a television (TV), a smart TV, an Internet-Protocol TV (IPTV), a smartphone, a personal computer, a laptop, a tablet, a wearable electronic device, or any other media device with a capability to receive, decode, and play content from over-the-air broadcast signals via cable or satellite networks, or from internet-based communication signals.

The display device 104 may include suitable logic, circuitry, and interfaces that may be configured to display video content that may be received from the media source 106. The display device 104 may be realized through several known technologies such as, but not limited to, a Liquid Crystal Display (LCD) display, a Light Emitting Diode (LED) display, a plasma display, or an Organic LED (OLED) display technology, or other display devices. In accordance with an embodiment, the display device 104 may refer to a display screen of a see-through display, a projection-based display, an electro-chromic display, or a transparent display.

The media source 106 may include suitable logic, circuitry, and interfaces that may be configured to transmit media content, such as audio/video content to the electronic apparatus 102. In an embodiment, the media source 106 may be implemented as a storage device that may be configured to store first audio content and corresponding video content related to the first audio content. Examples of such implementation of the media source 106 may include, but are not limited to, a Pen Drive, a Flash USB Stick, a Hard Disk Drive (HDD), a Solid-State Drive (SSD), and/or a Secure Digital (SD) card. In another embodiment, the media source 106 may be implemented as a media streaming server, which may transmit the first audio content and the corresponding video content to the electronic apparatus 102, via the communication network 118. In another embodiment, the media source 106 may be an TV tuner, such as an ATSC tuner, which may be configured to receive digital TV (DTV) signals from an over-the-air broadcast network and extract the first audio content and the corresponding video content from the received DTV signal. Thereafter, the media source 106 may transmit the extracted first audio content and the corresponding video content to the electronic apparatus 102.

In FIG. 1, the media source 106 and the electronic apparatus 102 are shown as two separate devices. However, the present disclosure may not be so limiting and in some embodiments, the functionality of the media source 106 may be incorporated in its entirety or at least partially in the electronic apparatus 102, without departing from the scope of the present disclosure.

The personal listening device 110 may include suitable logic, circuitry, and interfaces that may be configured to receive second audio content from the electronic apparatus 102 and play the received second audio content. The second audio content may be a modified version of the first audio content and may allow the first user 108 with the hearing disability to optimally hear the second audio content. Examples of the personal listening device 110 may include, but are not limited to, an over-head headphone, an in-ear headphone, a clip-on headphone, a bone-conduction headphone, a hearing aid, virtual reality googles, or a head-mounted wearable (such as a smart glass, a head-mounted display (e.g., a Virtual/Augmented/Mixed Reality headset). In an exemplary embodiment, the personal listening device 110 may be a wireless headphone which may rely on wireless communication protocols, such as Wi-Fi, Bluetooth®, or Bluetooth® Low Energy (BLE), to receive the second audio content from the electronic apparatus 102.

In an embodiment, the personal listening device 110 may include a microphone to capture voice content of the first user 108 and an input device to receive inputs from the first user 108. Examples of the input device may include, but are not limited to, a keypad, a knob, a touch screen, a touchpad, a gesture controller, or a voice-controlled input device. In another embodiment, the input device may be communicatively coupled to the personal listening device 110 through a wireless network. In such an implementation, the input device may be one of: a smartphone, a joystick, a game controller, or any other device which can be wirelessly paired with the personal listening device 110.

The image-capture device 112 may include suitable logic, circuitry, and interfaces that may be configured to capture an image of the listening environment 100. For example, the image may be captured to detect a worn state of the personal listening device 110 and/or whether the first user 108 with the hearing disability is the wearer of the personal listening device 110 in the detected worn state. In an embodiment, the image-capture device 112 may be communicatively coupled to the electronic apparatus 102 through the communication network 118. In another embodiment, the image-capture device 112 may be included in the electronic apparatus 102. Examples of the image-capture device 112 may include, but are not limited to, an image sensor, a wide-angle camera, an action camera, a closed-circuit television (CCTV) camera, a camcorder, a digital camera, camera phones, and/or other image capture devices.

The audio reproductive system 116 may include suitable logic, circuitry, and interfaces that may be configured to receive the first audio content (i.e. original source audio) from the electronic apparatus 102 and play the received first audio content for the users (such as the second user 114) with normal hearing levels in the listening environment 100. In an embodiment, the audio reproductive system 116 may be communicatively coupled to the electronic apparatus 102 through a wired or a wireless network. In another embodiment, the audio reproductive system 116 may be an internal speaker system of the electronic apparatus 102. The audio reproductive system 116 may include, for example, a set of internal speakers, a wireless speaker, a smart speaker, a wired speaker, a woofer, a sub-woofer, a tweeter, a soundbar, a loudspeaker, an optical audio device, and the like. In an exemplary embodiment, the audio reproductive system 116 may correspond to a surround sound system with a particular speaker layout/configuration, such as a 5:1 or 2:1 speaker configuration.

The communication network 118 may include a communication medium through which two or more of the electronic apparatus 102, the display device 104, the media source 106, the personal listening device 110, the image-capture device 112, and the audio reproductive system 116 may communicate with each other. The communication network 118 may be a wired or wireless communication network. Examples of the communication network 118 may include, but are not limited to, Internet, a Wireless Fidelity (Wi-Fi) network, a Personal Area Network (PAN), a Local Area Network (LAN), or a Metropolitan Area Network (MAN).

Various devices in the listening environment 100 may be configured to connect to the communication network 118, in accordance with various wired and wireless communication protocols. Examples of such wired and wireless communication protocols may include, but are not limited to, at least one of a Transmission Control Protocol and Internet Protocol (TCP/IP), User Datagram Protocol (UDP), Hypertext Transfer Protocol (HTTP), File Transfer Protocol (FTP), Zig Bee, EDGE, IEEE 802.11, light fidelity (Li-Fi), 802.16, IEEE 802.11s, IEEE 802.11g, multi-hop communication, wireless access point (AP), device to device communication, cellular communication protocols, and Bluetooth (BT) communication protocols.

In operation, the electronic apparatus 102 may receive the first audio content from the media source 106. In some embodiments, the electronic apparatus 102 may detect the first user 108 with the hearing disability as a wearer of the personal listening device 110. In an embodiment, the electronic apparatus 102 may control the image-capture device 112 to capture an image of the listening environment 100 which may include the first user 108 and the personal listening device 110. Based on the captured image, the electronic apparatus 102 may detect the first user 108 as the wearer of the personal listening device 110. For example, the electronic apparatus 102 may locally implement a facial recognition method on the image to detect the first user 108 and then use a trained deep neural network (DNN) to determine whether the detected first user 108 is the wearer of the personal listening device 110. In another embodiment, the electronic apparatus 102 may control the personal listening device 110 to capture a voice input from the wearer of the personal listening device 110. Thereafter, the electronic apparatus 102 may generate a voice profile (which may include digital audio fingerprints) based on the voice input and may compare the generated voice profile with a group of stored voice profiles of users. Based on such comparison, the electronic apparatus 102 may detect the first user 108 as the wearer of the personal listening device 110.

The electronic apparatus 102 may retrieve an audio enhancement profile, which may be associated with the first user 108 (or the detected first user 108). The audio enhancement profile may include a representation of hearing levels (in decibels (dB), for example) across a broad range of different pitches or audible frequencies for humans. For example, the audio enhancement profile may be audiogram, which may include a hearing curve of the first user 108 for both the left ear and the right ear. Based on the retrieved audio enhancement profile, the electronic apparatus 102 may modify one or more features of the first audio content. For example, one of such features may be the hearing levels (dB) for a range of audio frequencies associated with the first audio content. In case the audio enhancement profile indicates that the hearing level (in dB) of the first user 108 for 1000 Hz±250 Hz band is lower than a required threshold, sound amplitude levels of the first audio content for the 1000 Hz±250 Hz band may be increased to improve the hearing level. Other examples of such features may include, but are not limited to, an amplitude of a number of audio frames of the first audio content, a dynamic range of the first audio content, amplitude levels of speech frames in the first audio content, and a regulation speed for adjustment in gain levels for audio frames of the first audio content. Further details on the modification of the feature(s) are provided in FIG. 3, FIG. 4, and FIG. 5, for example.

The electronic apparatus 102 may generate the second audio content based on the modification of the first audio content. The second audio content may be an enhanced version of the first audio content and may be optimized according to conditions of hearing impairment of the first user 108. Such conditions may be reflected through datapoints, such as hearing levels, in the audio enhancement profile of the first user 108.

Once the second audio content is generated, the electronic apparatus 102 may share the generated second audio content with the personal listening device 110. Upon reception from the electronic apparatus 102, the personal listening device 110 may control playback of the second audio content for the first user 108. In some embodiments, the electronic apparatus 102 may control the audio reproductive system 116 to play the first audio content concurrently while the second audio content is played on the personal listening device 110 for a shared listening experience. For example, when the first user 108 hears the selectively enhanced second audio content through the personal listening device 110, the second user 114 may concurrently hear the first audio content through the audio reproductive system 116.

Modifications, additions, or omissions may be made to FIG. 1 without departing from the scope of the present disclosure. For example, the listening environment 100 may include more or fewer elements than those illustrated and described in the present disclosure.

Figure 2:
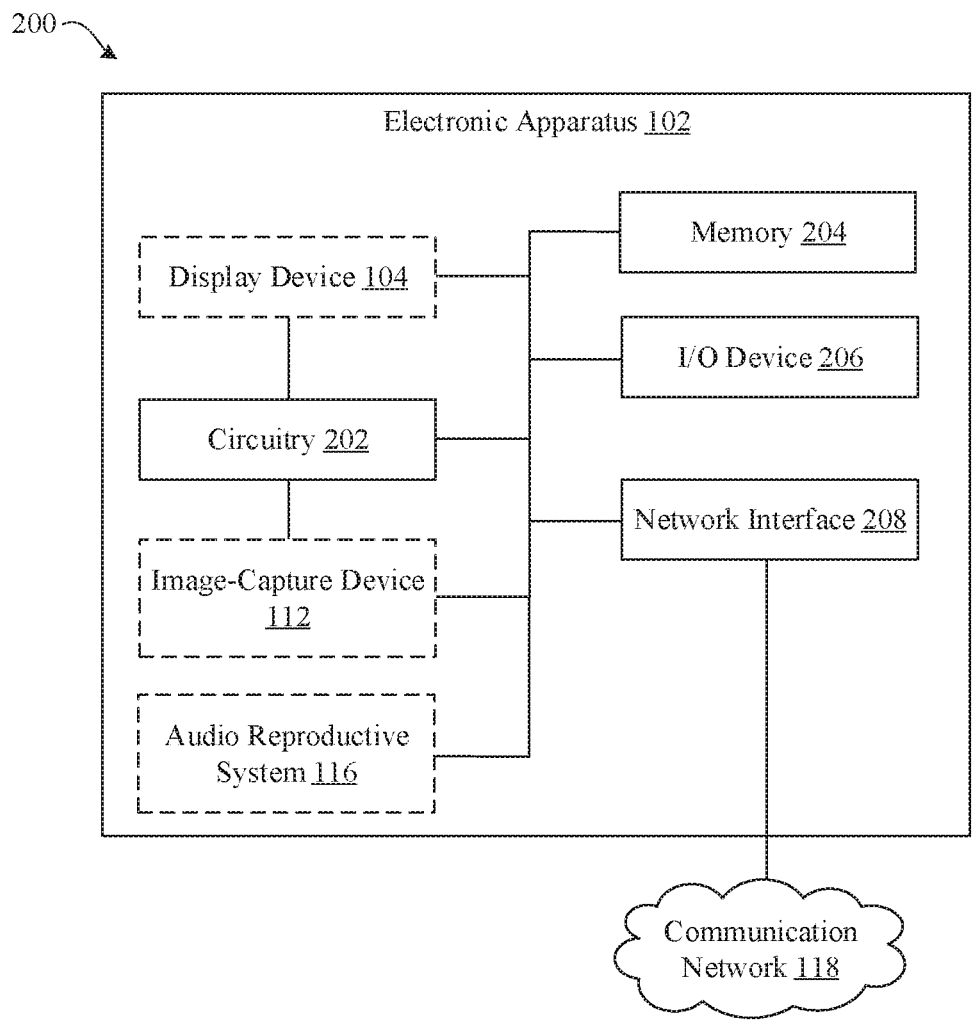
FIG. 2 is a block diagram that illustrates an exemplary electronic apparatus to provide enhanced audio content for a user with a hearing disability, in accordance with an embodiment of the disclosure.

FIG. 2 is a block diagram that illustrates an exemplary electronic apparatus to provide enhanced audio content for a user with a hearing disability, in accordance with an embodiment of the disclosure. FIG. 2 is explained in conjunction with elements from FIG. 1. With reference to FIG. 2, there is shown a block diagram 200 of the electronic apparatus 102. The electronic apparatus 102 may include circuitry 202, a memory 204, an input/output (I/O) device 206, and a network interface 208. In at least one embodiment, the electronic apparatus 102 may also include the display device 104, the image-capture device 112, and the audio reproductive system 116.

The circuitry 202 may include suitable logic, circuitry, and interfaces that may be configured to execute program instructions associated with different operations to be executed by the electronic apparatus 102. The circuitry 202 may include one or more specialized processing units, which may be implemented as an integrated processor or a cluster of processors that perform the functions of the one or more specialized processing units, collectively. The circuitry 202 may be implemented based on a number of processor technologies known in the art. Examples of implementations of the circuitry 202 may be an x86-based processor, a Graphics Processing Unit (GPU), a Reduced Instruction Set Computing (RISC) processor, an Application-Specific Integrated Circuit (ASIC) processor, a Complex Instruction Set Computing (CISC) processor, a microcontroller, a central processing unit (CPU), and/or other computing circuits.

The memory 204 may include suitable logic, circuitry, and interfaces that may be configured to store the program instructions to be executed by the circuitry 202. In at least one embodiment, the memory 204 may store files, such as the first audio content, the second audio content, and the video content. The memory 204 may also store user information for users who may be associated with the listening environment 100 and who may access the electronic apparatus 102. For example, the user information may include voice profiles, facial recognition information, or audio enhancement profiles for the first user 108 and the second user 114. Examples of implementation of the memory 204 may include, but are not limited to, Random Access Memory (RAM), Read Only Memory (ROM), Electrically Erasable Programmable Read-Only Memory (EEPROM), Hard Disk Drive (HDD), a Solid-State Drive (SSD), a CPU cache, and/or a Secure Digital (SD) card.

The I/O device 206 may include suitable logic, circuitry, and interfaces that may be configured to receive an input and provide an output based on the received input. The I/O device 206 which includes various input and output devices, may be configured to communicate with the circuitry 202. Examples of the I/O device 206 may include, but are not limited to, a touch screen, a keyboard, a mouse, a joystick, a microphone, a display device (such as the display device 104), or a button.

The network interface 208 may include suitable logic, circuitry, and interfaces that may be configured to facilitate a communication among the circuitry 202, the display device 104, the media source 106, the image-capture device 112, and/or the audio reproductive system 116, via the communication network 118. The network interface 208 may be implemented by use of various known technologies to support wired or wireless communication of the electronic apparatus 102 with the communication network 118. The network interface 208 may include, but is not limited to, an antenna, a radio frequency (RF) transceiver, one or more amplifiers, a tuner, one or more oscillators, a digital signal processor, a coder-decoder (CODEC) chipset, a subscriber identity module (SIM) card, or a local buffer circuitry.

The network interface 208 may be configured to communicate via wireless communication with networks, such as the Internet, an Intranet or a wireless network, such as a cellular telephone network, a wireless local area network (LAN), and a metropolitan area network (MAN). The wireless communication may use one or more of a plurality of communication standards, protocols and technologies, such as Global System for Mobile Communications (GSM), Enhanced Data GSM Environment (EDGE), wideband code division multiple access (W-CDMA), Long Term Evolution (LTE), code division multiple access (CDMA), time division multiple access (TDMA), Bluetooth, Wireless Fidelity (Wi-Fi) (such as IEEE 802.11a, IEEE 802.11b, IEEE 802.11g or IEEE 802.11n), voice over Internet Protocol (VoIP), light fidelity (Li-Fi), Worldwide Interoperability for Microwave Access (Wi-MAX), a protocol for email, instant messaging, and a Short Message Service (SMS).

The functions or operations executed by the electronic apparatus 102, as described in FIG. 1, may be performed by the circuitry 202. Operations executed by the circuitry 202 are described in detail, for example, in FIGS. 3, 4, 5, and 6.

Figure 3:
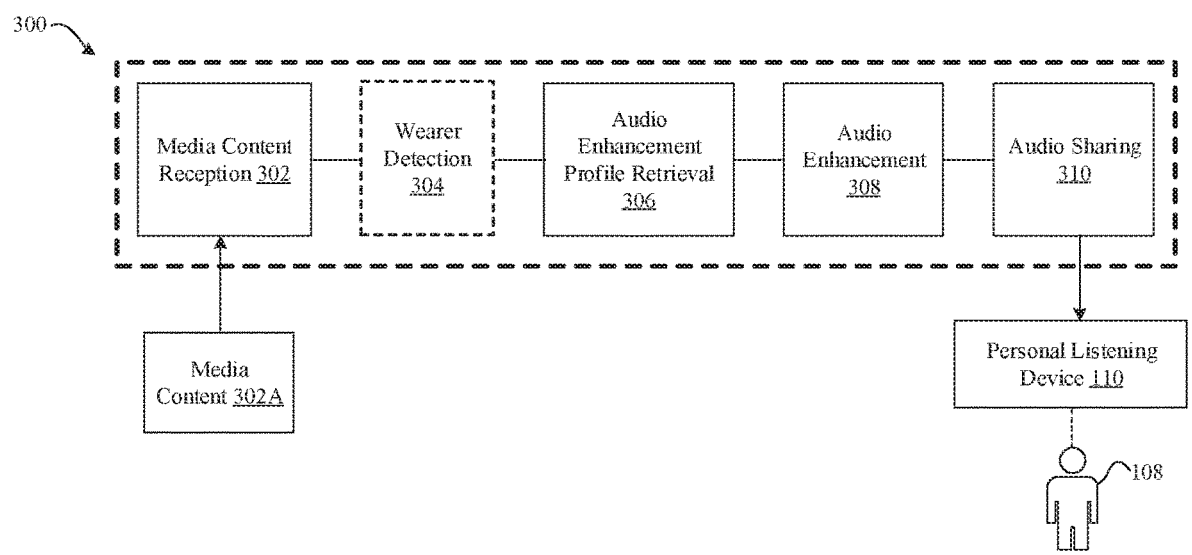
FIG. 3 is a diagram that illustrates exemplary operations to provide enhanced audio content for a user with a hearing disability, in accordance with an embodiment of the disclosure.

FIG. 3 is a diagram that illustrates exemplary operations to provide enhanced audio content for a user with a hearing disability, in accordance with an embodiment of the disclosure. FIG. 3 is explained in conjunction with elements from FIG. 1 and FIG. 2. With reference to FIG. 3, there is shown a block diagram 300 that illustrates exemplary operations from 302 to 310, as described herein. The exemplary operations illustrated in the block diagram 300 may start at 302 and may be performed by any computing system, apparatus, or device, such as by the electronic apparatus 102 of FIG. 1 or FIG. 2. Although illustrated with discrete blocks, the exemplary operations associated with one or more blocks of the block diagram 300 may be divided into additional blocks, combined into fewer blocks, or eliminated, depending on implementation of the exemplary operations.

At 302, media content 302A may be received. The circuitry 202 may receive the media content 302A from the media source 106. The received media content 302A may include first audio content and/or video content associated with the first audio content. As one example, the media content 302A may be a television program which may include a video and audio associated with the video. As another example, the media content 302A may be a radio show or a podcast which may only include audio.

At 304, wearer detection may be performed. The circuitry 202 may detect the first user 108 with the hearing disability as the wearer of the personal listening device 110. Various embodiments are described herein for detection of the first user 108 as the wearer of the personal listening device 110.

In an embodiment, the circuitry 202 may control the image-capture device 112 to capture an image of the listening environment 100 which may include the first user 108 and the personal listening device 110. Based on the captured image, the circuitry 202 may detect the first user 108 as the wearer of the personal listening device 110. For example, the circuitry 202 may locally implement a facial recognition method on the image to detect the first user 108 and then use a trained DNN to determine whether the detected first user 108 is the wearer of the personal listening device 110.

In another embodiment, the circuitry 202 may control the personal listening device 110 to capture a voice input from the wearer of the personal listening device 110 and the circuitry 202 may generate a voice profile (which may include digital audio fingerprints) based on the voice input. Thereafter, the circuitry 202 may compare the generated voice profile with a group of stored voice profiles of users and based on such comparison, the circuitry 202 may detect the first user 108 as the wearer of the personal listening device 110.

In another embodiment, the circuitry 202 may control the display device 104 to render a User Interface (UI) that includes a list of registered user profiles as user-selectable options. Through an input device associated with the personal listening device 110, the circuitry 202 may receive a selection of a registered user profile associated with the first user 108. The registered user profile may include information associated with the hearing disability of the first user 108. Based on such selection, the wearer of the personal listening device 110 may be detected as the first user 108.

At 306, an audio enhancement profile may be retrieved from the memory 204. The audio enhancement profile may be associated with the first user 108 (or the detected first user 108 at 304 with a hearing disability). The audio enhancement profile may include a representation of hearing levels (in decibels (dB)) across a broad range of pitches or audible frequencies for humans. For example, the audio enhancement profile may be represented through an audiogram, which may include a hearing curve of the first user 108 for both the left ear and the right ear. An example of the audiogram as the audio enhancement profile is provided in FIG. 5.

In case the audio enhancement profile is unavailable for the first user 108 (or the detected first user 108), the audio enhancement profile may be created, as described herein. The circuitry 202 may control the personal listening device 110 to sequentially play a set of test tones at a corresponding set of audible frequencies. The loudness of each test tone may increase while the respective test tone is played on the personal listening device 110. This may be done to allow the first user 108 (or the detected first user 108) of the personal listening device 110 to decide a loudness level up to which a respective test tone is clearly audible to the first user 108. The circuitry 202 may receive a set of user inputs while the set of test tones is played sequentially on the personal listening device 110. Each user input of the set of user inputs may indicate a hearing threshold level (in dB) for the respective test tone. Based on the received set of user inputs, the circuitry 202 may generate a hearing curve on an audiogram as the audio enhancement profile for the first user 108 (or the detected first user 108).

At 308, audio enhancement may be performed for the first user 108. For such enhancement, the circuitry 202 may modify one or more features of the first audio content based on the retrieved audio enhancement profile (obtained at 302C). Examples of such features may include, but are not limited to, an amplitude of a number of audio frames of the first audio content, amplitude levels of a band of audible frequencies of the first audio content, a dynamic range of the first audio content, amplitude levels of speech frames in the first audio content, and a regulation speed for adjustment in gain levels for audio frames of the first audio content.

In one scenario, the first user 108 may suffer from a high-frequency hearing loss (typically 2000 Hz or higher). As a result, the first user 108 may face difficulty in understanding voices of females, children, birds' singing, or other high-pitched sounds. Alternatively, the first user 108 may suffer from a low-frequency hearing loss. As a result, the first user 108 may face difficulty in hearing conversations within groups of people or in noisy environments and in places where background noise is present, or in listening to bass sounds of music. In such a scenario, the circuitry 202 may determine a type of hearing loss associated with the first user 108 (or the detected first user 108) based on the audio enhancement profile. Based on the determined type of hearing loss, the circuitry 202 may determine a band of audible frequencies for which hearing levels of the first user 108 (or the detected first user 108) are below a threshold hearing level (in dB). Thereafter, the circuitry 202 may selectively amplify amplitude levels of a number of audio frames of the first audio content which include the determined band of audible frequencies. The selective amplification may correspond to the modification of a first feature of the first audio content.

In another scenario, the first user 108 may be detected to have a mild hearing loss, which may shrink a hearing range to 60 dB to 70 dB and may reduce a dynamic range of hearing of the first user 108. In comparison, a user with normal hearing levels may have a hearing range of about 100 dB between threshold and an uncomfortable loudness level. Herein, the dynamic range may be defined as a ratio of the strongest, or loudest part of audio to the weakest or softest part of the audio. In such a scenario, the circuitry 202 may determine a first dynamic range of the first audio content and a second dynamic range of hearing of the first user 108 (or the detected first user 108) based on the enhancement profile. Thereafter, the circuitry 202 may use compressors, expanders, or noise gates to modify the first dynamic range of the first audio content so that the difference in the modified first dynamic range and the second dynamic range is a minimum. In other words, the dynamic range of the audio content may be modified so that it fits into the dynamic range of the hearing of the first user 108. The modification of the first dynamic range may correspond to the modification of a second feature of the first audio content.

In another scenario, the first user 108 may suffer from a severe-to-profound hearing loss, in which cochlear high-frequency region may be so severely damaged that it may not be possible to restore audibility of audio samples (which contain high frequency signals) by means of conventional amplification. In such a scenario, the audibility may be achieved by a shift of high frequency signal components of the first audio content to low frequency signal components. The circuitry 202 may extract the high frequency signal components of the first audio content and may transform the extracted high frequency signal components to the low frequency signal components. The transformation of the extracted high frequency signal components may correspond to the modification of a third feature of the first audio content.

The circuitry 202 may generate second audio content based on the modification of the first audio content. The second audio content may be the modified form of the first audio content and may be adapted to address deficiencies associated with the hearing disability of the first user 108. Specifically, the second audio content may improve one or more of speech intelligibility, hearing comfort, sound quality, audibility across a broad range of frequencies, or perception of natural loudness of sound associated with the first audio content.

At 310, audio content may be shared with the personal listening device 110. The circuitry 202 may share the generated second audio content with the personal listening device 110, via a wireless network, such as Bluetooth® or Wi-Fi. In an embodiment, the circuitry 202 may control the audio reproductive system 116 to play the first audio content concurrently with a playback of the second audio content on the personal listening device 110 for a shared listening experience. Therefore, when the first user 108 hears the second audio content through the personal listening device 110, the second user 114 may concurrently hear the first audio content through the audio reproductive system 116. As both the first audio content and the second audio content are played concurrently, both users (the first user 108 and the second user 114) may be able to enjoy the shared listening experience in a common listening environment.

Figure 4:
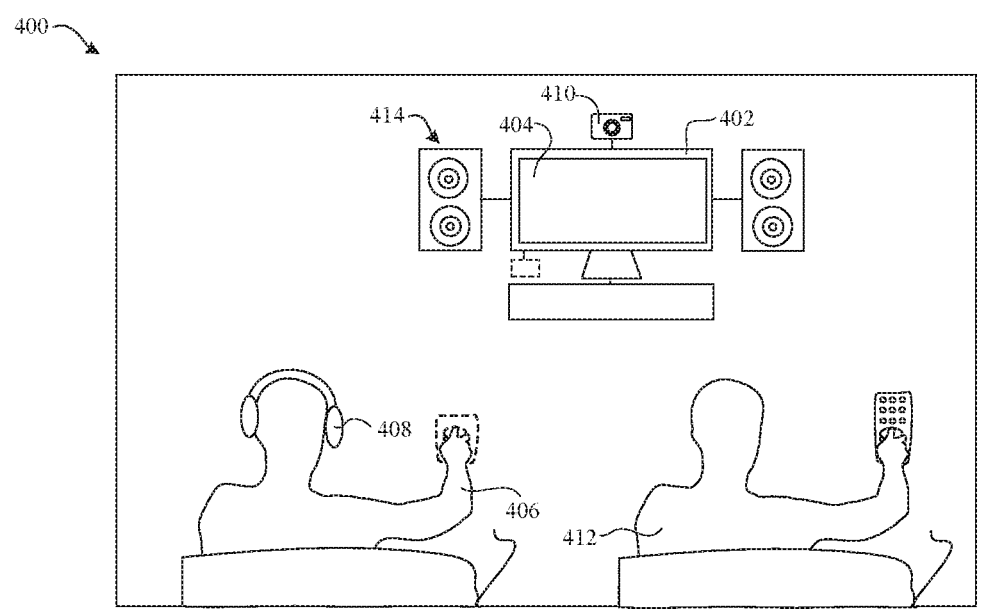
FIG. 4 is a diagram that illustrates an exemplary scenario to enhance audio content for a user with a hearing impairment, in accordance with an embodiment of the disclosure.

FIG. 4 is a diagram that illustrates an exemplary scenario to enhance audio content for a user with a hearing impairment, in accordance with an embodiment of the disclosure. FIG. 4 is explained in conjunction with elements from FIGS. 1, 2, and 3. With reference to FIG. 4, there is shown an exemplary scenario 400. In the exemplary scenario 400, there is shown a television 402 and a display panel 404 of the television, a first user 406, a personal listening device 408, an image-capture device 410, a second user 412, and an audio reproductive system 414. Herein, the television 402, the display panel 404, the personal listening device 408, the image-capture device 410, and the audio reproductive system 414 may be exemplary implementations of the electronic apparatus 102, the display device 104, the personal listening device 110, the image-capture device 112, and the audio reproductive system 116, respectively.

The television 402 may receive media content through the media source 106, such as an ATSC tuner. The media content may include first audio content and video content associated with the first audio content. The television 402 may control the display panel 404 to display the video content associated with the first audio content. For the first user 406 with hearing disability, the television 402 may generate the second audio content (as described in the FIG. 3) based on modification of one or more features of the first audio content. The second audio content may be a modified form of the first audio content and may be adapted to address hearing deficiencies of the first user 406.

Typically, when the television 402 wirelessly shares the second audio content with the personal listening device 408, the playback of the second audio content may be delayed (e.g., in few tens to hundreds of milliseconds) as compared to the playback of the video content on the display panel 404. This may be attributed to wireless audio processing methods for encoding or decoding of the second audio content and/or wireless sharing methods for the second audio content. In case of the video playback, processing methods for the video content may incur a delay that may be visually unnoticeable to the human eyes during the display of the video content, especially as compared to the delay associated with the playback of the second audio content. This may create a lip-sync issue for the first user 406. Also, in case the audio reproductive system 414 is wired to the television 402 and plays the first audio content, the delay associated with the playback of the first audio content may be considerably negligible as compared to the delay associated with the playback of the second audio content. In such a case, the sound of the first audio content may mix with the sound of the second audio content, causing the first user 406 to hear an echo.

In order to mitigate such issues, the circuitry 202 may compute a first processing delay associated with the encoding of the second audio content for a wireless sharing with the personal listening device 408. The circuitry 202 may also compute a second processing delay associated with the decoding of the second audio content at the personal listening device 408. Thereafter, the circuitry 202 may calibrate a time of the display of the video content on the display panel 404 based on the computed first processing delay and the second processing delay. For example, such calibration may include a shift in the time of the display of the video content by a time equivalent to a sum of the computed first processing delay and the second processing delay. Such calibration may synchronize the playback of the video content with the playback of the second audio content on the personal listening device. Additionally, the circuitry 202 may also calibrate a time of playback of the first audio content through the audio reproductive system 414 to synchronize with the playback of the video content 304B on the display panel 404.

Figure 5:
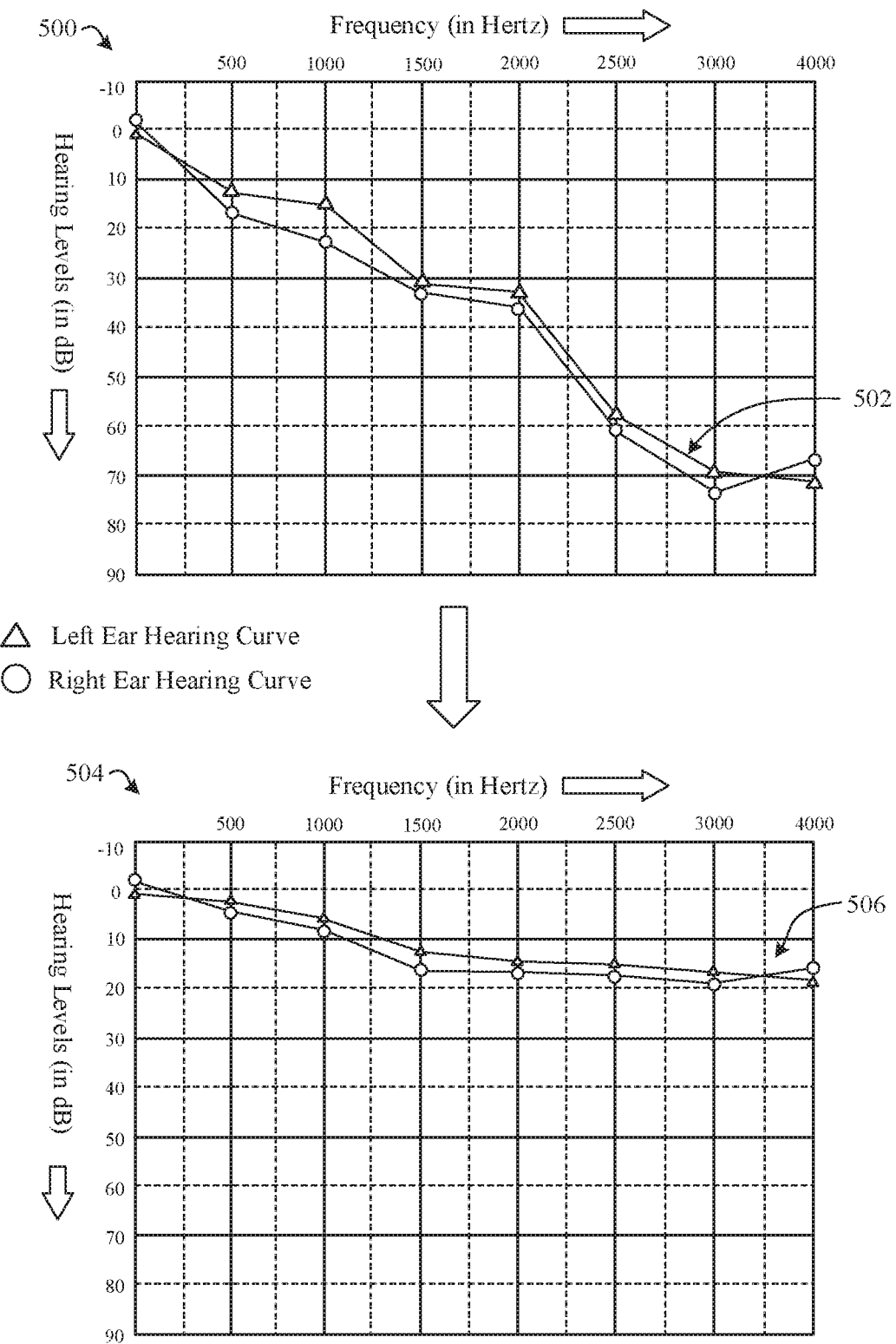
FIG. 5 is a diagram that illustrates a scenario for audio enhancement for a user with a hearing disability based on an audiogram of the user, in accordance with an embodiment of the disclosure.

FIG. 5 is a diagram that illustrates a scenario for audio enhancement for a user with a hearing disability based on an audiogram of the user, in accordance with an embodiment of the disclosure. FIG. 5 is explained in conjunction with elements from FIGS. 1, 2, 3, and 4. With reference to FIG. 5, there is shown a first audiogram 500 that includes a hearing curve 502 for the first user 108 with the hearing disability and a second audiogram 504 that includes a hearing curve 506 of another user with normal hearing levels across a broad range of audible frequencies.

In the first audiogram 500, the hearing curve 502 of the first user 108 indicates hearing levels as normal for an audible frequency band of 0 Hertz (i.e. Hz) to 250 Hz. However, for an audible frequency band beyond 250 Hz, the hearing curve 502 of the first user 108 indicates a degradation in the hearing levels, especially for audible frequencies beyond 2000 Hz. The first audiogram 500 may be referred to as the audio enhancement profile of the first user 108. In order to correct the hearing levels of the first user 108, the circuitry 202 may compare the hearing curve 502 of the first user 108 with the hearing curve 506 of another user with the normal hearing levels. Based on the comparison, the circuitry 202 may determine one or more features of the first audio content to be modified to generate the second audio content. For example, in this case, the circuitry 202 may determine a number of audible frequency bands for which signal energy levels may have to be selectively amplified to calibrate the hearing levels (in dB) for the first user 108. Thereafter, the circuitry 202 may determine a number of audio frames of the first audio content as a feature (as one of the determined one or more features) based on a determination that the determined number of audio frames contains the determined number of audible frequency bands. Thereafter, the circuitry 202 may selectively amplify the determined number of audio frames of the first audio content to generate the second audio content. The second audio content may be shared with the personal listening device 110 for playback.

In case the first user 108 suffers from a hearing disability of a left or right ear, the circuitry 202 may select a first audio portion as one of a left channel audio or a right channel audio of the first audio content based on a determination that the hearing curve 502 for the first user 108 indicates a hearing impairment condition for one of the left ear or the right ear of the first user 108. The circuitry 202 may generate the second audio content based on a modification of one or more features (e.g., hearing levels (in dB)) of the selected first audio portion of the first audio content.

Figure 6:
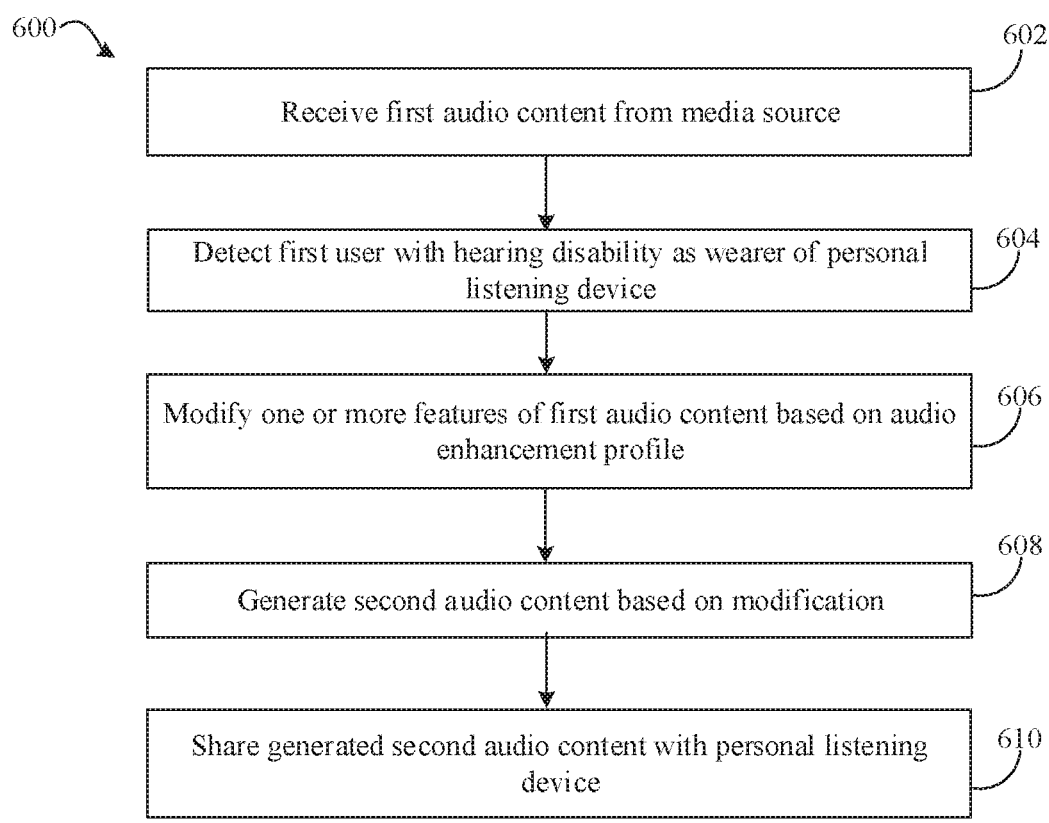
FIG. 6 is a flowchart that illustrates exemplary operations to provide enhanced audio content for a user with a hearing impairment, in accordance with an embodiment of the disclosure.

FIG. 6 is a flowchart that illustrates exemplary operations to provide enhanced audio content for a user with a hearing impairment, in accordance with an embodiment of the disclosure. FIG. 6 is explained in conjunction with elements from FIGS. 1, 2, 3, 4, and 5. With reference to FIG. 6, there is shown a flowchart 600. The operations from 602 to 610 may be implemented by any computing system, such as by the electronic apparatus 102 of FIG. 1 or FIG. 2. The operations may start at 602 and may proceed to 604.

At 602, first audio content may be received from the media source 106. In at least one embodiment, the circuitry 202 may be configured to receive the first audio content from the media source 106.

At 604, the first user 108 with the hearing disability may be detected as a wearer of the personal listening device 110. In at least one embodiment, the circuitry 202 may be configured to detect the first user 108 with the hearing disability as the wearer of the personal listening device 110.

At 606, one or more features of the first audio content may be modified based on the audio enhancement profile associated with the first user 108 (or the detected first user 108). In at least one embodiment, the circuitry 202 may be configured to modify one or more features of the first audio content based on the audio enhancement profile 606 associated with the first user 108 (or the detected first user 108).

At 608, the second audio content may be generated based on the modification. In at least one embodiment, the circuitry 202 may be configured to generate the second audio content based on the modification.

At 610, the generated second audio content may be shared with the personal listening device 110. In at least one embodiment, the circuitry 202 may be configured to share the generated second audio content with the personal listening device 110. Control may pass to end.

Although the flowchart 600 is illustrated as discrete operations, such as 602, 604, 606, 608 and 610. However, in certain embodiments, such discrete operations may be further divided into additional operations, combined into fewer operations, or eliminated, depending on the implementation without detracting from the essence of the disclosed embodiments.

Various embodiments of the disclosure may provide a non-transitory computer readable medium and/or storage medium having stored thereon, instructions executable by a machine and/or a computer to operate an electronic apparatus, such as the electronic apparatus 102. The instructions may cause the machine and/or computer to perform operations that include receiving first audio content from the media source 106. In one or more embodiments, the operations may also include detecting the first user 108 with the hearing disability as the wearer of the personal listening device 110. The operations may further include modifying one or more features of the first audio content based on the audio enhancement profile associated with the first user 108 (or the detected first user 108). The operations may further include generating the second audio content based on the modification and sharing the generated second audio content with the personal listening device 110.

Exemplary aspects of the disclosure may include an electronic apparatus (such as the electronic apparatus 102 of FIG. 1) that includes circuitry (such as the circuitry 202) that may be communicatively coupled to a personal listening device (such as the personal listening device 110 of FIG. 1). The circuitry may be configured to receive first audio content from a media source (such as the media source 106 of FIG. 1) and detect a first user (such as the first user 104) with a hearing disability as a wearer of the personal listening device. The circuitry may be further configured to modify one or more features of the first audio content based on an audio enhancement profile associated with the detected first user. By way of example, and not limitation, the one or more features may include an amplitude of a number of audio frames of the first audio content, amplitude levels of a band of audible frequencies of the first audio content, a dynamic range of the first audio content, amplitude levels of speech frames in the first audio content, a regulation speed for adjustment in gain levels for audio frames of the first audio content, and the like. Thereafter, the circuitry may be configured to generate second audio content based on the modification and share the generated second audio content with the personal listening device.

In accordance with an embodiment, the circuitry may be further configured to control an audio reproductive system (such as the audio reproductive system 114 of FIG. 1) to play the first audio content concurrently with a playback of the second audio content on the personal listening device for a shared listening experience. For example, the audio reproductive system may include one or more of: an external wireless speaker, a set of internal speakers, an external wired speaker, a sub-woofer, a tweeter, a soundbar, or an optical audio device.

In accordance with an embodiment, the electronic apparatus may include an image-capture device (such as the image-capture device 112) communicatively coupled to the circuitry. The circuitry may be configured to control the image-capture device to capture an image of a listening environment (such as the listening environment 100) which includes the first user and the personal listening device and detect the first user as the wearer of the personal listening device based on the captured image.

In accordance with an embodiment, the audio enhancement profile may be an audiogram which may include a hearing curve of the first user for both the left ear and the right ear of the first user. The circuitry may be configured to compare the hearing curve of the first user with a reference hearing curve of a second user with normal hearing levels and determine the one or more features of the first audio content for the modification based on the comparison.

In accordance with an embodiment, wherein the circuitry may be further configured to select a first audio portion as one of a left channel audio or a right channel audio of the first audio content based on a determination that the hearing curve for the first user indicates a hearing impairment condition for one of the left ear or the right ear of the first user. Thereafter, the circuitry may modify the one or more features of the selected first audio portion of the first audio content and generate the second audio content based on the modification.

In accordance with an embodiment, the circuitry may be configured to control the personal listening device to sequentially play a set of test tones at a corresponding set of audible frequencies. The loudness of each test tone in the set of test tones may increase while the respective test tone is played on the personal listening device. Thereafter, the circuitry may receive a set of user inputs while the set of test tones is played sequentially on the personal listening device. Each user input may indicate a hearing threshold level for the respective test tone. Based on the received set of user inputs, the circuitry may generate a hearing curve on an audiogram as the audio enhancement profile for the first user.

In accordance with an embodiment, the electronic apparatus may include a display device (such as the display device 104) configured to display video content that may be associated with the first audio content. The circuitry may be configured to compute a first processing delay associated with encoding of the second audio content for a wireless sharing with the personal listening device and compute a second processing delay associated with decoding of the second audio content at the personal listening device. Thereafter, the circuitry may be further configured to calibrate a time of the display of the video content to synchronize with a playback of the second audio content on the personal listening device based on the computed first processing delay and the second processing delay.

The present disclosure may be realized in hardware, or a combination of hardware and software. The present disclosure may be realized in a centralized fashion, in at least one computer system, or in a distributed fashion, where different elements may be spread across several interconnected computer systems. A computer system or other apparatus adapted to carry out the methods described herein may be suited. A combination of hardware and software may be a general-purpose computer system with a computer program that, when loaded and executed, may control the computer system such that it carries out the methods described herein. The present disclosure may be realized in hardware that comprises a portion of an integrated circuit that also performs other functions.

The present disclosure may also be embedded in a computer program product, which comprises all the features that enable the implementation of the methods described herein, and which when loaded in a computer system is able to carry out these methods. Computer program, in the present context, means any expression, in any language, code or notation, of a set of instructions intended to cause a system with information processing capability to perform a particular function either directly, or after either or both of the following: a) conversion to another language, code or notation; b) reproduction in a different material form.

While the present disclosure is described with reference to certain embodiments, it will be understood by those skilled in the art that various changes may be made, and equivalents may be substituted without departure from the scope of the present disclosure. In addition, many modifications may be made to adapt a situation or material to the teachings of the present disclosure without departure from its scope. Therefore, it is intended that the present disclosure is not limited to the embodiment disclosed, but that the present disclosure will include all embodiments that fall within the scope of the appended claims.

What is claimed is:

1. An electronic apparatus, comprising:
    circuitry communicatively coupled to a personal listening device, wherein the circuitry is configured to:
        receive first audio content from a media source;
        detect a first user with a hearing disability as a wearer of the personal listening device;
        modify one or more features of the first audio content based on an audio enhancement profile associated with the detected first user;
        generate second audio content based on the modification;
        share the generated second audio content with the personal listening device;
        share the received first audio content with an audio reproductive system;
        control the audio reproductive system to play the first audio content concurrently with a playback of the second audio content on the personal listening device for a shared listening experience, wherein
            the audio reproductive system is different from the personal listening device, and
            the audio enhancement profile is an audiogram comprising a hearing curve of the first user for both a left ear and a right ear of the first user; and
        select an audio portion as one of a left channel audio or a right channel audio of the first audio content based on a determination that the hearing curve for the first user indicates a hearing impairment condition for one of the left ear or the right ear of the first user.

2. The electronic apparatus according to claim 1, wherein the audio reproductive system comprises one or more of an external wireless speaker, a set of internal speakers, an external wired speaker, a sub-woofer, a tweeter, a soundbar, or an optical audio device.

3. The electronic apparatus according to claim 1, further comprising an image-capture device communicatively coupled to the circuitry, wherein the circuitry is further configured to:
    control the image-capture device to capture an image of a listening environment comprising the first user and the personal listening device; and
    detect the first user as the wearer of the personal listening device based on the captured image.

4. The electronic apparatus according to claim 1, wherein the circuitry is further configured to: compare the hearing curve of the first user with a reference hearing curve of a second user with normal hearing levels; and determine the one or more features of the first audio content for the modification based on the comparison.

5. The electronic apparatus according to claim 1, wherein the circuitry is further configured to: modify the one or more features of the selected first audio portion of the first audio content; and generate the second audio content based on the modification.

6. The electronic apparatus according to claim 1, wherein the circuitry is further configured to:
    control the personal listening device to sequentially play a set of test tones at a corresponding set of audible frequencies,
        wherein loudness of each test tone in the set of test tones increases while the respective test tone is played on the personal listening device;
    receive a set of user inputs while the set of test tones is played sequentially on the personal listening device, wherein each user input indicates a hearing threshold level for the respective test tone; and
    generate the hearing curve on the audiogram as the audio enhancement profile for the first user based on the received set of user inputs.

7. The electronic apparatus according to claim 1, further comprising a display device configured to display video content that is associated with the first audio content.

8. The electronic apparatus according to claim 7, wherein the circuitry is further configured to:
    compute a first processing delay associated with encoding of the second audio content for a wireless sharing with the personal listening device;
    compute a second processing delay associated with decoding of the second audio content at the personal listening device; and
    calibrate a time of the display of the video content to synchronize with the playback of the second audio content on the personal listening device based on the computed first processing delay and the second processing delay.

9. The electronic apparatus according to claim 1, wherein the one or more features comprises an amplitude of a number of audio frames of the first audio content, amplitude levels of a band of audible frequencies of the first audio content, a dynamic range of the first audio content, amplitude levels of speech frames in the first audio content, or a regulation speed for adjustment in gain levels for the audio frames of the first audio content.

10. The electronic apparatus according to claim 1, wherein the circuitry is further configured to:

control the personal listening device to capture a voice input from the wearer of the personal listening device; and detect the first user as the wearer of the personal listening device based on the voice input.

11. The electronic apparatus according to claim 1, wherein the circuitry is further configured to determine whether the detected first user is wearing the personal listening device.

12. A method, comprising:
receiving first audio content from a media source;
detecting a first user with a hearing disability as a wearer of a personal listening device;
modifying one or more features of the first audio content based on an audio enhancement profile associated with the detected first user;
generating second audio content based on the modification;
sharing the generated second audio content with the personal listening device;
sharing the received first audio content with an audio reproductive system;
controlling the audio reproductive system to play the first audio content concurrently with a playback of the second audio content on the personal listening device for a shared listening experience, wherein
the audio reproductive system is different from the personal listening device, and
the audio enhancement profile is an audiogram comprising a hearing curve of the first user for both a left ear and a right ear of the first user; and
selecting an audio portion as one of a left channel audio or a right channel audio of the first audio content based on a determination that the hearing curve for the first user indicates a hearing impairment condition for one of the left ear or the right ear of the first user.

13. The method according to claim 12, further comprising:
controlling an image-capture device to capture an image of a listening environment comprising the first user and the personal listening device; and
detecting the first user as the wearer of the personal listening device based on the captured image.

14. The method according to claim 12, further comprising: comparing the hearing curve of the first user with a reference hearing curve of a second user with normal hearing levels; and determining the one or more features of the first audio content for the modification based on the comparison.

15. The method according to claim 12, further comprising: modifying the one or more features of the selected first audio portion of the first audio content; and generating the second audio content based on the modification.

16. The method according to claim 12, further comprising:

controlling the personal listening device to sequentially play a set of test tones at a corresponding set of audible frequencies,
wherein loudness of each test tone in the set of test tones increases while the respective test tone is played on the personal listening device;
receiving a set of user inputs while the set of test tones is played sequentially on the personal listening device, wherein each user input indicates a hearing threshold level for the respective test tone; and
generating the hearing curve on the audiogram as the audio enhancement profile for the first user based on the received set of user inputs.

17. The method according to claim 12, further comprising:
computing a first processing delay associated with encoding of the second audio content for a wireless sharing with the personal listening device;
computing a second processing delay associated with decoding of the second audio content at the personal listening device; and
calibrating a time of a display of a video content associated with the first audio content for synchronizing with the playback of the second audio content on the personal listening device based on the computed first processing delay and the second processing delay.

18. An electronic apparatus, comprising:
circuitry communicatively coupled to a personal listening device, wherein the circuitry is configured to:
retrieve an audio enhancement profile associated with a first user;
receive first audio content from a media source;
modify one or more features of the first audio content based on the retrieved audio enhancement profile;
generate second audio content based on the modification;
share the generated second audio content with the personal listening device;
share the received first audio content with an audio reproductive system;
control the audio reproductive system to play the first audio content concurrently with a playback of the second audio content on the personal listening device, wherein
the audio reproductive system is different from the personal listening device, and
the audio enhancement profile is an audiogram comprising a hearing curve of the first user for both a left ear and a right ear of the first user; and
select an audio portion as one of a left channel audio or a right channel audio of the first audio content based on a determination that the hearing curve for the first user indicates a hearing impairment condition for one of the left ear or the right ear of the first user.

* * * * *